(12) United States Patent
Birkel et al.

(10) Patent No.: US 7,135,166 B2
(45) Date of Patent: Nov. 14, 2006

(54) HAIR STYLING STICK CONTAINING POLYETHYLENE GLYCOLS OF DIFFERENT MOLECULAR WEIGHTS

(75) Inventors: Susanne Birkel, Glashutten (DE); Harald Wendel, Ober-Ramstadt (DE); Michael Franzke, Rossdorf (DE); Bernd Stein, Hoesbach (DE); Manuela Hannich, Darmstadt (DE)

(73) Assignee: Wella AG, Darmstadt (DE)

( * ) Notice: Subject to any disclaimer, the term of this patent is extended or adjusted under 35 U.S.C. 154(b) by 294 days.

(21) Appl. No.: 10/125,824

(22) Filed: Apr. 19, 2002

(65) Prior Publication Data

US 2002/0164298 A1   Nov. 7, 2002

Related U.S. Application Data

(63) Continuation-in-part of application No. 09/954,581, filed on Sep. 17, 2001, now abandoned.

(30) Foreign Application Priority Data

Sep. 22, 2000  (DE) ................. 100 47 038
Oct. 31, 2001  (EP) ................. 01125978

(51) Int. Cl.
*A61K 8/00* (2006.01)
*A61K 8/18* (2006.01)
*A61K 8/72* (2006.01)
*A61K 6/00* (2006.01)
*A61K 8/02* (2006.01)

(52) U.S. Cl. ............... 424/70.11; 424/401; 424/76.3; 424/78.31

(58) Field of Classification Search ........... 424/70.1, 424/70.31, 78.31, 70.11, 76.3, 401
See application file for complete search history.

(56) References Cited

U.S. PATENT DOCUMENTS

| 2,309,722 | A | 2/1943 | Wilkes |
| 4,938,954 | A | 7/1990 | Gross |
| 5,500,218 | A | 3/1996 | Kischka et al. |
| 5,690,924 | A | 11/1997 | Keil et al. |
| 6,241,978 | B1 | 6/2001 | Schlaeger |
| 6,338,858 | B1 | 1/2002 | Dupuis et al. |

FOREIGN PATENT DOCUMENTS

| EP | 0 301 197 | 2/1989 |
| EP | 0 865 786 A1 | 9/1998 |
| GB | 1 563 824 | 4/1980 |

*Primary Examiner*—San-Ming Hui
(74) *Attorney, Agent, or Firm*—Michael J. Striker

(57) ABSTRACT

The hair styling stick contains from 30 to 55 percent by weight of one or more polyethylene glycols with a molecular weight of from 2500 to 5000 g/mol; and from 40 to 70 percent by weight of at least one other polyethylene glycol with a molecular weight of from 570 to 800 g/mol together with cosmetic ingredients. In preferred embodiments the hair styling stick contains from 30 to 55 percent by weight of one or more polyethylene glycols with a molecular weight of from 2500 to 5000 g/mol; from 15 to 35 percent by weight of one or more polyethylene glycols with a molecular weight of from 850 to 1600 g/mol, from 15 to 35 percent by weight of one or more liquid polyethylene glycols with a molecular weight of from 570 to 800 g/mol and additional cosmetic ingredients, as needed. The additional cosmetic ingredients can include an aqueous or organic solvent, emulsifier, perfume or fragrance, dye, preservative and/or pearlescence-imparting agent.

15 Claims, No Drawings

HAIR STYLING STICK CONTAINING POLYETHYLENE GLYCOLS OF DIFFERENT MOLECULAR WEIGHTS

CROSS-REFERENCE

This is a continuation-in-part of U.S. patent application, Ser. No. 09/954,581, filed on Sep. 17, 2001 now abandoned.

BACKGROUND OF THE INVENTION

The subject matter of the present invention is a hair styling stick having a composition of fixed wax-like consistency and comprising a combination of at least one high molecular weight polyethylene glycol with at least one low molecular weight polyethylene glycol, and especially a combination of three different polyethylene glycols with three different molecular weights.

Styling wax compositions are known products for hair treatment. They are especially used for bringing short to middle length hair into a stylish shape. For example, hairstyles in the form of high-bang hairstyles, combed forehead hairstyles and the so-called "dirty-look" or "spiky-look" hairstyles are possible. Various different shapes and textures may also be produced for each hairstyle. Conventional styling wax products are usually available in pans. Portions of these products may be taken out of the pans with fingers. The wax is then spread on the surface of the hand where it softens because of the body heat transmitted from the hand. The otherwise too solid wax may then be distributed in the hair because of this softening. After working the wax into the hair, it hardens again and the formed hairstyle is stable and has a wet look.

The disadvantage of this type of wax composition is that the hands of the user come into extensive contact with the wax and subsequently must be cleaned. There is therefore a need to be fulfilled by the present invention for a product, which has the product properties of a pan wax, i.e. imparts luster, care and hold to the hair, but is in the form of another type of composition, in which the fingers and/or hand surfaces do not need to be wet. A suitable form for this new composition would be a hair styling stick. This new composition has a series of requirements. The composition need not be too hard and must be spread easily on the hair in direct application without softening it by heating. At the same time it should not be too soft, since otherwise the desired set and hold of the hairstyle is not attained. The portions that can be rubbed off of the stick must not be too small and the consistency of the stick must not be too brittle.

Besides the composition must not be too sticky, since otherwise hair may adhere to the styling stick, when the stick is stroked over the hair.

Conventional styling sticks are usually based on hydrophobic waxes, fats and oils. They contain a large proportion of hydrophobic materials, such as fat or animal waxes, fatty acid esters, fatty alcohols, etc. This sort of product has the disadvantage that it is only poorly washable from the hair and causes a comparatively high load or stress on the hair.

European Patent Document EP 0 301 197 A 1 discloses a hair wax containing a combination of conventional high molecular weight polyethylene glycols (MW=3000 to 5000), ethoxylated and hydrogenated castor oil and low molecular weight polyethylene glycols (MW=100 to 300). This reference only describes pan products, but no styling sticks. The manufacture of hair styling sticks with completely satisfactory product properties is not possible with the combination of two polyethylene glycols of such very different molecular weights as described in EP 0 301 197 A 1, The resulting sticks have a too great and too brittle consistency because of the very different molecular weights. Also inhomogeneities are formed in the wax mass after cooling, which make the stick noticeably softer in its interior than on the outside.

Known pomade rods or bars for treating hair comprising 60 percent by weight polyethylene glycol 4000 and 40 percent by weight ethyl hexanediol are described in Janistyn, "Handbuch der Kosmetika und Riechstoff [Handbook of Cosmetics and Fragrances]", Vol. 3, p. 325 (1973). Hair treated with the pomade rods however has neither a satisfactory luster nor sufficient shape stability nor a satisfactory permanence. Also ethyl hexanediol is an irritating substance, which should not be included in cosmetic products.

SUMMARY OF THE INVENTION

It is an object of the present invention to provide a hair styling stick that provides luster, hair care and hold to the hair treated with it, but does not have the disadvantageous properties of a pan wax.

It has now been found that the requirements are fulfilled by a hair styling stick with a composition of solid, wax-like consistency, which contains a combination of a high molecular weight polyethylene glycol and a low molecular weight polyethylene glycol of predetermined molecular weights and, in an even better manner, by a hair styling stick containing a combination of three different polyethylene glycols of different molecular weights.

According to the invention the hair styling stick with a solid, wax-like or waxy composition contains, and, in some embodiments, consists of:

(A) at least one polyethylene glycol with a molecular weight of from 2500 to 5000 g/mol;

(B) at least one polyethylene glycol with a molecular weight of from 370 to 800 g/mol; and, as needed or optionally, water, a univalent alcohol having from one to five carbon atoms, a polyvalent alcohol having from one to five carbon atoms, emulsifiers, perfumes, dyestuffs and/or pearlescence-imparting pigments.

The combination of polyethylene glycols with the stated molecular weights is outstandingly suitable for making a hair styling product in the form of a stick.

DESCRIPTION OF THE PREFERRED EMBODIMENTS

According to a particularly preferred embodiment of the invention the hair styling stick with a solid, wax-like or waxy composition contains:

(A) from 30 to 55 percent by weight of at least one polyethylene glycol with a molecular weight of from 2500 to 5000 g/mol;

(B) from 15 to 35 percent by weight of at least one polyethylene glycol with a molecular weight of from 850 to 1600 g/mol; and (C) from 15 to 35 percent by weight of at least one polyethylene glycol with a molecular weight of from 370 to 800 g/mol; and, as needed or optionally, water, a univalent alcohol having from one to five carbon atoms, a polyvalent alcohol having from one to five carbon atoms, emulsifiers, perfumes, dyestuffs and/or pearlescence-imparting pigments.

The preferred embodiments of the hair styling stick with the three different polyethylene glycols are characterized by an especially greater homogeneity than the embodiments with only two different polyethylene glycols.

The high molecular weight polyethylene glycols (A) are solid, wax-like or waxy at room temperatures (20° C. to 25° C.). The hair styling stick preferably contains the high molecular weight polyethylene glycol ingredient in a concentration of from 30 to 55 percent by weight, especially preferably from 35 to 45 percent by weight. The molecular weight amounts to from 2500 to 5000 g/mol, preferably from 2700 to 3500 g/mol. Polyethylene glycols have the formula: $H(OCH_2CH_2)_nOH$. Suitable high molecular weight polyethylene glycols are those with n=57 to 113, preferably with n=61 to 79, Suitable high molecular weight polyethylene glycols have the INCI names PEG-60 (n=60), PEG-75 (n=75), PEG-90 (n=90) and PEG-100 (n=100). PEG-50 and PEG-75 are especially preferred. Commercially obtained polyethylene glycols usually have a molecular weight distribution.

Suitable commercial products are e.g. polyglycol 3000 with a molecular weight of 2700 to 3000 or polyglycol 4000 of Clariant with a molecular weight of 3700 to 4500, The polyglycol 3000 is more preferable than the polyglycol 4000, since it leads to a styling stick that is too soft and deposits too large amounts of the composition on the hair.

The intermediate molecular weight ethylene glycols (B) are preferably soft wax-like substances at room temperatures (20° C. to 25° C.) with a solidification temperature of about 30 to 45° C. They are present in the composition in concentrations of preferably from 20 to 30%. Their molecular weights are preferably from 850 to 1200 g/mol. Polyethylene glycols have the general formula: $H(OCH_2CH_2)_nOH$. Suitable polyethylene glycols (B) are those with n=19 to 35, preferably with n=20 to 24. Suitable polyethylene glycols have the INCI-names PEG-20 (n=20) and PEG-32 (n=32). PEG-20 is particularly preferred. Commercial products generally have a molecular weight distribution. Suitable commercial products include e.g. polyglycol 1000 with a molecular weight of 950 to 1050 g/mol or polyglycol 1350 with a molecular weight of 1300 to 1400 g/mol or polyglycol 1500 with a molecular weight of 1400 to 1600 g/mol of Clariant. Polyglycol 1000 is most preferred as the ingredient B.

The lower molecular weight polyethylene glycols (C) are at least soft wax-like materials or preferably liquid at room temperatures (20° C. to 25° C.). They are present in the composition according to the invention in an amount of 15 to 35 percent by weight, especially preferably from 20 to 30 percent by weight. The molecular weights of the lower molecular weight polyethylene glycols amounted to from 370 to 800 g/mol, preferably from 400 to 640 g/mol. Suitable lower molecular weight polyethylene glycols have the formula: $H(OCH_2CH_2)_nOH$, wherein n=8 to 16, preferably n=9 to 14. Suitable low molecular weight polyethylene glycols have the INCI names PEG-8 (n=8), PEG-9 (n=9), PEG-10 (n=10), PEG-12 (n=12), PEG-14 (n=14) and PEG-16 (n=16). PEG-9 (n=9PEG-10 (n=10), PEG-12 (n=12) and PEG-14 (n=14) are particularly preferred. Suitable commercial products are e.g. polyglycol 400 with a molecular weight of 380 to 420 or polyglycol 600 of Clariant with a molecular weight of 570 to 630, The polyglycol 600 is more preferable than the polyglycol 400, since it leads to a combination for sticks that are too soft and deposit too large portions on the hair.

It has been shown that the styling stick has a poorer, coarser and more brittle consistency, the more different the molecular weights of the two polyethylene glycol ingredients are from each other in the case of the embodiments with two polyethylene glycols of different molecular weight. A comparison of the stick composition according to the invention with the composition disclosed in European Patent Document EP 0 301 197, which contains a polyglycol 200 (molecular weight 190 to 210 g/mol) that is of lower molecular weight than the lower molecular weight polyethylene glycols of the present invention shows that the prior art styling stick is essentially coarser and more brittle. This observed brittleness probably depends on the crystallization properties of the entire composition.

The making of the styling stick occurs in the usual manner. The components are mixed at high temperatures at which the higher molecular weight polyethylene glycol ingredient is present as a liquid. Subsequently it is cooled down, which usually occurs by means of an additional exterior cooling device. The higher molecular polyethylene glycols solidify whereby the crystallization occurs in an exothermic manner. It has been shown that the selection of the lower molecular weight polyethylene glycols has an influence on the crystallization behavior. The more the molecular weights of the lower molecular weight polyethylene glycols and the higher molecular weight polyethylene glycols are separated from each other, the coarser and more brittle is the styling stick.

On the other hand, the lower molecular weight polyethylene glycols should still be liquid at room temperatures, since otherwise product performance with respect to luster and the ability to spread on the hair is impaired. Polyethylene glycol 600 with a molar mass of 570 to 630 g/mol and a freezing point of from 15 to 22° C., i.e. just under room temperatures, is very suitable.

The weight ratio of the high molecular weight polyethylene glycols (A) to the sum total of both lower molecular weight polyethylene glycols (B) and (C) is preferably from 1:0.9 to 1:1.8, especially preferably from 1:1 to 1:1.6. The weight ratio of polyethylene glycol (B) to polyethylene glycol (C) amounts to preferably from 1:0.7 to 1:1.3, especially preferably from 1:0.8 to 1:1.2. The amount and type of additive ingredients are selected so that the dripping or liquifying point of the finished stick is preferably at least 40° C., especially in a range from 40 to 60° C., especially preferably in a range from 45 to 55° C.

The styling stick according to the invention permits individual hairstyling and desired treatments of individual hair strands. The product mass is easily spread on the hair, without contacting the product mass with hands or fingers. The hair treated with the styling stick has an outstanding luster. The set hairstyle has high shape stability. The hair is not loaded excessively and the product mass is easily washed from the hair.

In addition to the polyethylene glycol ingredients the styling stick according to the invention can also contain the following cosmetic additive ingredients:

solvents, such as water or a univalent or polyvalent C1- to C4-alcohols, such as ethanol, propanol, glycerol or glycols in an amount of up to 10 percent by weight, preferably from 0.1 to 8 percent by weight;

cosmetic dyestuffs in an amount of up to 6 percent by weight, preferably from 0.1 to 4 percent by weight, e.g. C.I. Pigment Red 4 (C.I. 12 085), C.I. Pigment Green (C.I. 74260), and!or C.I. Vat Blue 4 (C.I 69 800);

pearlescence-imparting pigments in an amount of up to 25 percent by weight, preferably from 1 to 20 percent by weight, e.g. those based on titanium dioxide/mica;

emulsifiers in an amount of up to 25 percent by weight, preferably from 0.1 to 18 percent by weight, e.g. hydrogenated and ethoxylated castor oil;

perfumes and fragrances in an amount of up to 2 percent by weight, preferably from 0.01 to 1 percent by weight;

preservatives in an amount of up to 1 percent by weight, preferably from 0.01 to 0.5 percent by weight, especially p-hydroxybenzoic acid ester, benzoic acid, salicylic acid, sorbic acid, mandelic acid, polyhexamethylene biguanidine hydrochloride or isothazolinone derivative compounds, of which the sorbic acid has proven especially suitable;

hydrophobic waxes, fats or oils, e.g. plant wax, animal wax or mineral wax, such as ozocerite; fatty acid esters, fatty alcohols in an amount of up to 5 percent by weight, preferably from 0.1 to 4 percent by weight;

film-forming polymers, such as polyvinyl pyrrolidone or vinyl pyrrolidone/vinyl acetate copolymers in an amount of up to 5 percent by weight, preferably from 0.1 to 4 percent by weight; and hair care substances, such as betaine, in an amount of up to 5 percent by weight, preferably from 0.01 to 4 percent by weight.

The manufacture of the styling stick occurs by melting and mixing the ingredients at an elevated temperature, at which the high molecular weight polyethylene glycols (A) are present in liquid form (e.g. at about 65 to 90° C.). Subsequently the uniform melt is cooled somewhat if necessary and filled in a package or container in the desired stick shape (stick sleeve) while it is still in liquid form. The product mass then solidifies under further cooling, preferably with an external cooling device (e.g. from 0 to 10° C.). The rapid cooling with the external cooling device produces a styling stick with a greater strength than with slower cooling without the external cooling device.

The usual materials for packaging the styling stick are used, especially plastics or metals. The geometric shape of the styling stick is not limited in any way. It can be in cylindrical form with a round or oval basic surface, however it can also have a basic triangular shape.

The application of the wax in stick form is very simple. The stick is pulled or drawn over the hair and portions of the product leave the stick. Luster, texture and/or hold are provided to the hair because of this application or treatment.

The following examples illustrate the claimed invention in further detail.

EXAMPLES

The styling sticks with the following compositions were made by melting and mixing the ingredients with stirring at about 85° C. After cooling to 65 to 70° C. the resulting mass for each styling stick was filled into a stick sleeve. The mass then solidified in the sleeve with cooling to 4° C.

| Example 1: Styling Stick | |
|---|---|
| 28.5 g | PEG-12 (polyglycol 600) |
| 28.5 g | PEG-20 (polyglycol 1000) |
| 43.0 g | PEG-60 (polyglycol 3000) |

| Example 2: Styling Stick | |
|---|---|
| 28.1 g | PEG-12 (polyglycol 600) |
| 28.0 g | PEG-20 (polyglycol 1000) |
| 43.0 g | PEG-60 (polyglycol 3000) |
| 0.5 g | water |
| 0.2 g | perfume |
| 0.1 g | betaine |
| 0.1 g | glycerol |

| Example 3: Styling Stick | |
|---|---|
| 29.4 g | PEG-12 (polyglycol 600) |
| 29.3 g | PEG-20 (polyglycol 1000) |
| 40.0 g | PEG-60 (polyglycol 3000) |
| 0.5 g | water |
| 0.3 g | PEG-25 hydrogenated castor oil |
| 0.3 g | perfume |
| 0.1 g | betaine |
| 0.1 g | ozocerite |

| Example 4: Styling Stick | |
|---|---|
| 27.75 g | PEG-12 (polyglycol 600) |
| 27.70 g | PEG-20 (polyglycol 1000) |
| 43.00 g | PEG-60 (polyglycol 3000) |
| 0.50 g | water |
| 0.30 g | PEG-25 hydrogenated castor oil |
| 0.30 g | perfume |
| 0.25 g | sorbic acid |
| 0.10 g | betaine |
| 0.10 g | ozocerite |

Unless otherwise indicated, all percentages are percentages by weight.

While the invention has been illustrated and described as embodied in a hair styling stick containing polyethylene glycols of different molecular weights, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A hair styling stick consisting of a solid composition, said solid composition containing 30 to 55 percent by weight of at least one polyethylene glycol with a molecular weight of from 2500 to 5000 g/mol and at least 15 percent by weight of at least one other polyethylene glycol with a molecular weight of from 570 to 800 g/mol.

2. The hair styling stick as defined in claim 1, wherein said solid composition contains from 40 to 70 percent by weight of said at least one other polyethylene glycol with said molecular weight of from 570 to 800 g/mol.

3. The hair styling stick as defined in claim 1, wherein said at least one other polyethylene glycol with said molecular weight of from 570 to 800 g/mol is liquid at room temperatures from 20 to 25° C.

4. The hair styling stick as defined in claim 1, wherein a weight ratio of said at least one polyethylene glycol with said molecular weight of from 2500 to 5000 g/mol to said at least one other polyethylene glycol with said molecular weight of from 570 to 800 g/mol amounts to from 1:0.9 to 1.8.

5. The hair styling stick as defined in claim 1, wherein said molecular weight of said at least one polyethylene glycol is from 2700 to 3500 g/mol.

6. The hair styling stick as defined in claim 1, wherein said molecular weight of said at least one other polyethylene glycol is from 570 to 640 g/mol.

7. The hair styling stick as defined in claim 1, containing from 35 to 45 percent by weight of said at least one polyethylene glycol with said molecular weight of from 2500 to 5000 g/mol.

8. The hair styling stick as defined in claim 6, containing from 52 to 60 percent by weight of said at least one other polyethylene glycol with said molecular weight of from 570 to 640 g/mol.

9. A hair styling stick consisting of a solid composition, said solid composition consisting of 30 to 55 percent by weight of at least one polyethylene glycol with a molecular weight of from 2500 to 5000 g/mol and from 40 to 70 percent by weight of at least one other polyethylene glycol with a molecular weight of from 570 to 800 g/mol.

10. A hair styling stick consisting of a solid composition, said solid composition consisting of
    from 30 to 55 percent by weight of at least one polyethylene glycol with a molecular weight of from 2500 to 5000 g/mol;
    from 40 to 70 percent by weight of at least one other polyethylene glycol with a molecular weight of from 570 to 800 g/mol; and
    at least one additional ingredient selected from the group consisting of water, univalent alcohols having from one to four carbon atoms, polyvalent alcohols having from one to four carbon atoms, cosmetic dyestuffs, pearlescence-imparting pigments, emulsifiers, perfumes, fragrances, preservatives, plant waxes, animal waxes, mineral waxes, fats, oils, film-forming polymers and betaine.

11. A hair styling stick consisting of a solid composition, said solid composition comprising
    from 30 to 55 percent by weight of at least one polyethylene glycol with a molecular weight of from 2500 to 5000 g/mol;
    from 15 to 35 percent by weight of at least one additional polyethylene glycol with a molecular weight of from 850 to 1600 g/mol; and
    from 15 to 35 percent by weight of at least one other polyethylene glycol with a molecular weight of from 570 to 800 g/mol.

12. The hair styling stick as defined in claim 11, wherein a weight ratio of said at least one polyethylene glycol with said molecular weight of from 2500 to 5000 g/mol to a sum total of said at least one additional polyethylene glycol with said molecular weight of 850 to 1600 g/mol and said at least one other polyethylene glycol with said molecular weight of from 570 to 800 g/mol amounts to from 1:0.9 to 1.8.

13. The hair styling stick as defined in claim 11, wherein a weight ratio of said at least one additional polyethylene glycol with said molecular weight of from 850 to 1600 g/mol to said at least one other polyethylene glycol with said molecular weight of from 570 to 800 g/mol amounts to from 1:0.7 to 1:1.3.

14. The hair styling stick as defined in claim 11, wherein said molecular weight of said at least one additional polyethylene glycol is from 850 to 1200 g/mol.

15. The hair styling stick as defined in claim 11, wherein said solid composition includes at least one additional ingredient selected from the group consisting of water, univalent alcohols having from one to four carbon atoms, polyvalent alcohols having from one to four carbon atoms, cosmetic dyestuffs, pearlescence-imparting pigments, emulsifiers, perfumes, fragrances, preservatives, plant waxes, animal waxes, mineral waxes, fats, oils, film-forming polymers and betaine.

\* \* \* \* \*